United States Patent [19]
Fogarty et al.

[11] Patent Number: 5,464,447
[45] Date of Patent: Nov. 7, 1995

[54] IMPLANTABLE DEFIBRILLATOR ELECTRODES

[75] Inventors: Thomas J. Fogarty, Portola Valley; Thomas A. Howell, Palo Alto, both of Calif.

[73] Assignee: Sony Corporation, Japan

[21] Appl. No.: 188,573

[22] Filed: Jan. 28, 1994

[51] Int. Cl.⁶ .................................................. A61N 1/05
[52] U.S. Cl. ......................................... 607/129; 128/642
[58] Field of Search ................. 607/115–121, 129–130, 607/132; 128/642

[56] References Cited

U.S. PATENT DOCUMENTS

| | | | |
|---|---|---|---|
| 4,291,707 | 9/1981 | Heilman et al. | 607/129 |
| 4,765,341 | 8/1988 | Mower et al. | 607/116 |
| 5,020,544 | 6/1991 | Dahl et al. | 607/129 |
| 5,042,463 | 8/1991 | Lekholm | 607/129 |
| 5,087,243 | 2/1992 | Avitall | 607/120 |
| 5,154,182 | 10/1992 | Moaddeb | 607/120 |
| 5,354,328 | 10/1994 | Doan et al. | 607/129 |

FOREIGN PATENT DOCUMENTS

| | | | |
|---|---|---|---|
| 0475027 | 3/1992 | European Pat. Off. | 607/129 |
| 2260564 | 7/1973 | Germany | 607/116 |

*Primary Examiner*—William E. Kamm
*Assistant Examiner*—Marianne Parker
*Attorney, Agent, or Firm*—Limbach & Limbach; Charles P. Sammut

[57] ABSTRACT

Improved implantable defibrillator electrodes and methods of implanting such electrodes are disclosed. One embodiment of the defibrillator electrodes includes a flexible conductive mesh and non-conductive mesh. Another embodiment of the defibrillator electrodes includes a flexible conductive mesh, a non-conductive mesh and an insulator therebetween. A third embodiment of the defibrillator electrode compensates for the shape of a human heart. Methods for implanting the defibrillator electrodes include rolling an electrode and inserting the rolled electrode into a subxiphoid opening while thorascopically observing the insertion and manipulation of the defibrillator electrode.

14 Claims, 6 Drawing Sheets

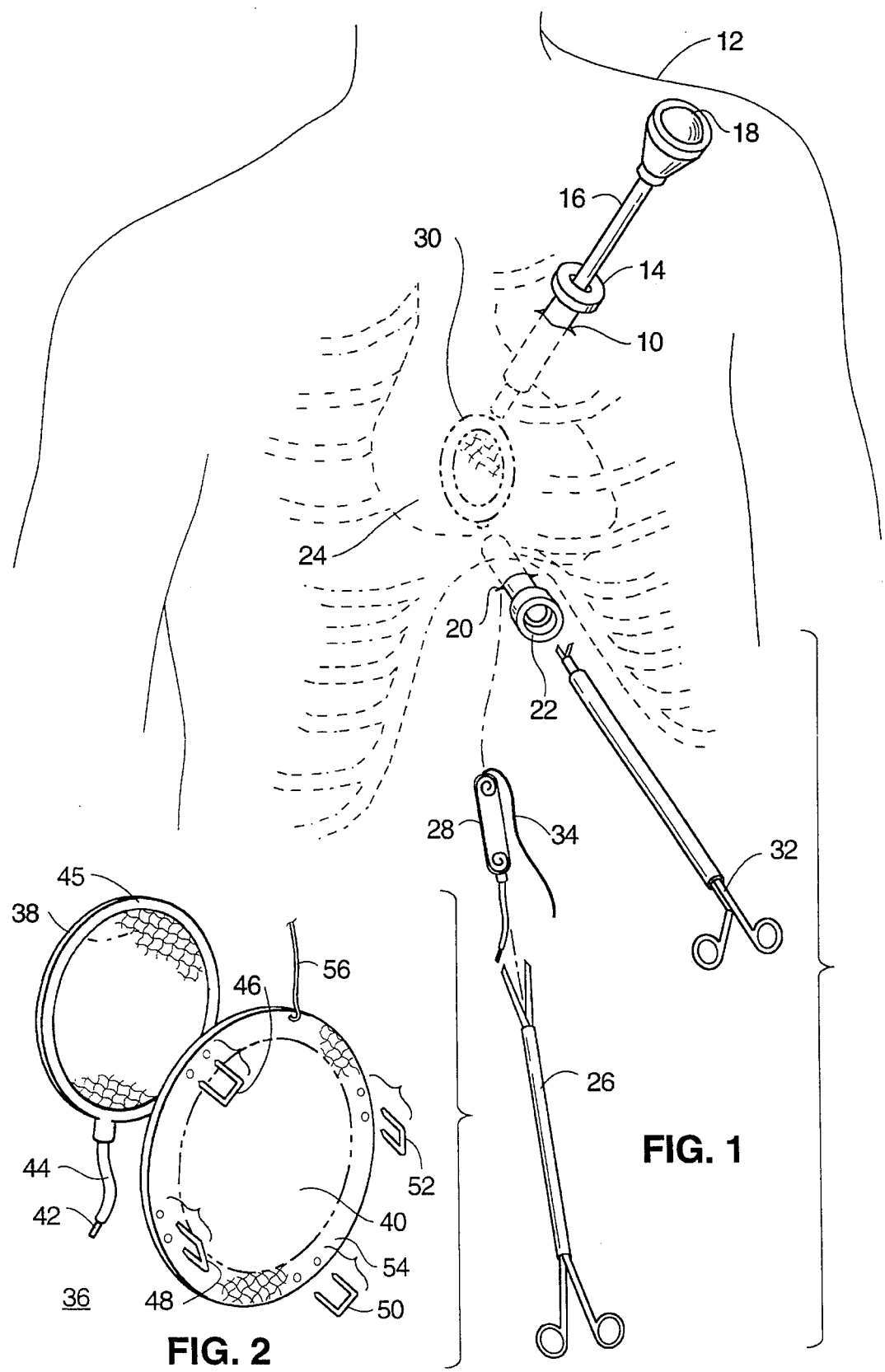

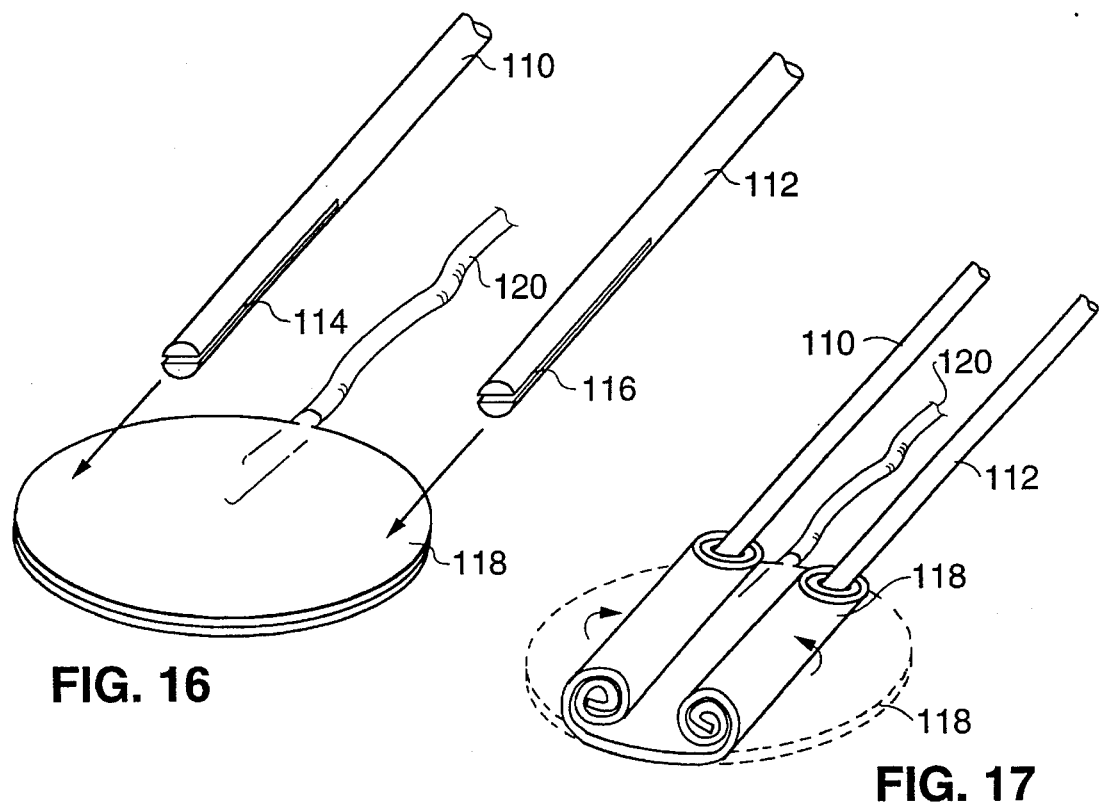
FIG. 16
FIG. 17
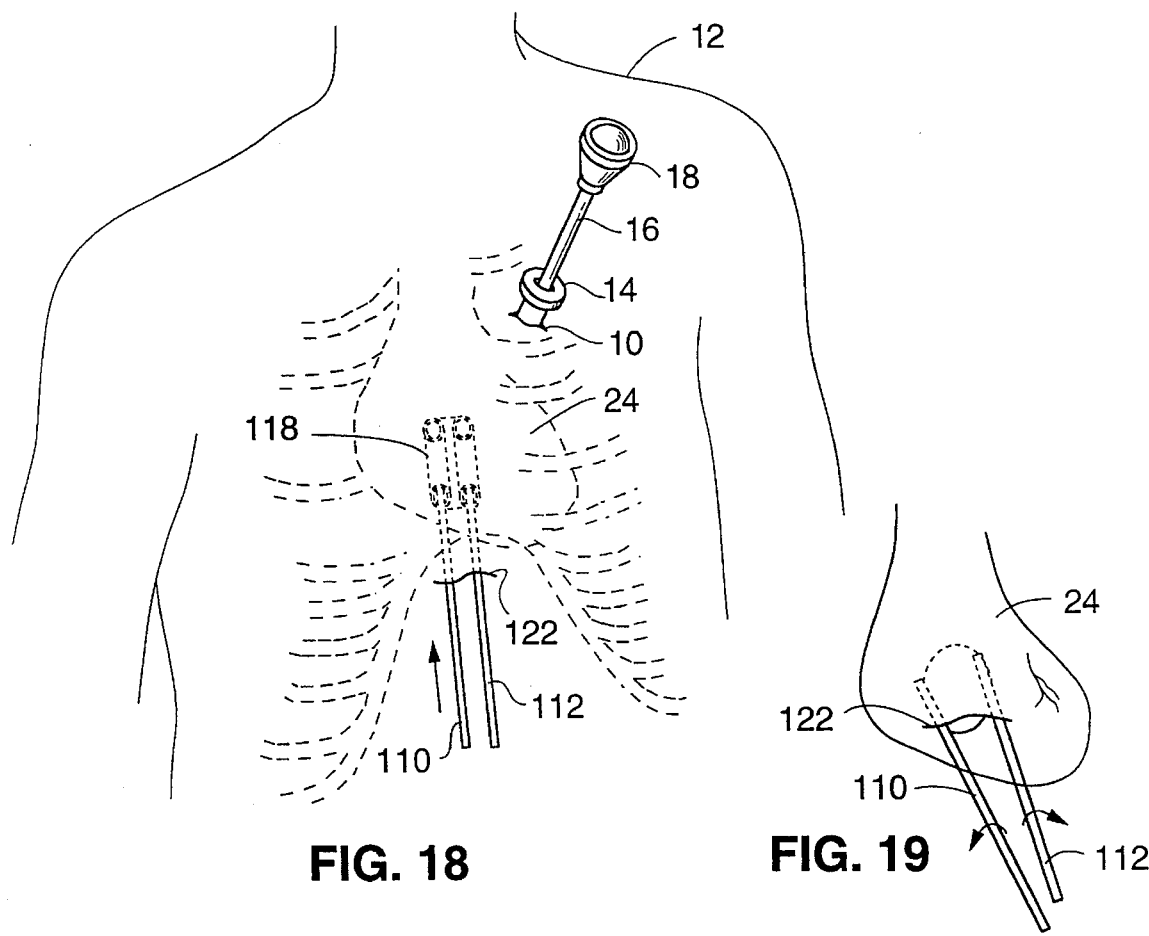
FIG. 18
FIG. 19

IMPLANTABLE DEFIBRILLATOR ELECTRODES

FIELD OF THE INVENTION

This invention relates generally to electrical defibrillation, and relates more specifically to particular types of implantable defibrillator electrodes and methods of implanting them with a minimal amount of surgery.

DISCUSSION OF THE PRIOR ART

It is well known in the field of cardiology that certain types of cardiac arrhythmias known as ventricular tachycardia and fibrillation can be effectively treated by the application of electrical energy in the form of pulses to the heart to defibrillate the fibrillating tissues. Such defibrillation may be achieved by the application of such pulses through electrodes applied to the chest of a patient or applied directly to a patient's heart tissue, if patient's chest is open during surgery.

More recent improvements have led to the development of implantable defibrillators which automatically monitor the heart for arrhythmia and initiate defibrillation when arrhythmia is sensed. Such devices typically incorporate electrodes which are located either next to the heart or on an intravascular catheter, or both. Because the electrodes are closer to the heart tissue, than is the case with electrical paddles applied to the chest, implanted defibrillators require less energy to defibrillate than is required with external electrical paddles. Furthermore, energy supplied to electrodes applied to the chest usually cause unwanted contractions of chest wall muscles.

However, major surgery such as median sternotomy or lateral thoracotomy, is generally necessary to implant defibrillator electrodes. These surgical procedures can be very traumatic to a patient, and may have adverse side effects such as surgical complications, or even worse, mortality. In particular, both median sternotomy and lateral thoracotomy cause great patient discomfort during recovery. Furthermore the act of retracting the sternum can cause painful rib fractures as well as possible Brachial Plexus nerve impingement. Retracting the ribs, during a lateral thoracotomy, can also cause painful rib fractures. Because of these risks, some patients who might otherwise benefit from an implantable defibrillator do not undergo surgery given the heretofore risk to benefit ratio.

SUMMARY OF THE INVENTION

The method of the present invention provides access to the pericardium and heart through small multiple opening sites (under 12 millimeter diameter) made in the chest and xiphisternal area. In particular a subxiphoid opening, such as an incision or puncture, is used for insertion of defibrillator electrodes, while an opening, such as an incision or puncture, between the 2nd rib and the 6th rib of a patient is used for observation via a thoracoscope. The exact location of the incision or opening is dependent upon a patient's particular anatomy. A trocar is inserted into the latter opening to facilitate the insertion and withdrawal of the thoracoscope and/or instrumentation. The defibrillator electrodes may also be manipulated through this latter opening site. A third opening may be used for additional instrumentation and thoracoscopic observation as well as the later placement of a chest drainage tube. Another method of the present invention first prepares a defibrillator electrode for insertion into a patient by rolling the defibrillator electrode with a pair of handles and then using the handles to insert the rolled defibrillator electrode into a patient through an opening in the patient.

One aspect of the apparatus of the present invention is directed toward a defibrillator electrode which includes a conductive wire mesh with a silicone backing, the silicone backing having a tail attached thereto. This allows the electrode to be pulled into place and then manipulated within the pericardium. The base of the tail can also be used as an attachment point for single point fixation. After proper placement of the electrode, permanent fixation with titanium staples is performed. In an alternative embodiment of a defibrillator electrode a silicone insulator is positioned between a conductive wire mesh and a nonconductive mesh. A tail is attached to the nonconductive mesh.

The embodiments of the defibrillator electrodes of the present invention allow placement of each electrode through very small openings and further allow fixation of the electrodes with metal staples without electrical current exchange problems.

Another aspect of the apparatus of the present invention is directed toward a carrier for use in transporting a rolled defibrillator electrode through an opening for implantation of the electrode within a patient.

Yet another aspect of the apparatus of the present invention is directed toward an apparatus for rolling a defibrillator electrode and transporting the rolled defibrillator electrode through a small opening within a patient.

These and other objects of the methods and apparatus of the invention will become more apparent when viewed in light of the following detailed description and accompanying drawing.

BRIEF DESCRIPTION OF THE DRAWING

FIG. 1 is a front perspective view of the upper chest region of a human body, with parts thereof shown in phantom, illustrating the preferred methods of access for implanting defibrillator electrodes;

FIG. 2 is an exploded perspective view of a first preferred embodiment of a defibrillator electrode of the present invention;

FIG. 16 is a perspective view illustrating in part an alternative method of rolling and retaining a defibrillator electrode for placement within a patient;

FIG. 17 is a perspective view illustrating in part the alternative method illustrated in FIG. 16 of rolling and retaining a defibrillator electrode for placement within a patient.

FIG. 18 is a diagrammatic perspective view further detailing the method illustrated in FIGS. 16 and 17;

FIG. 19 is a diagrammatic perspective view illustrating in part the alternative method illustrated in FIGS. 16, 17 and 18 of rolling, relining, inserting and positioning a defibrillator electrode within a patient.

DETAILED DESCRIPTION OF THE PREFERRED EMBODIMENTS

Figure 3:
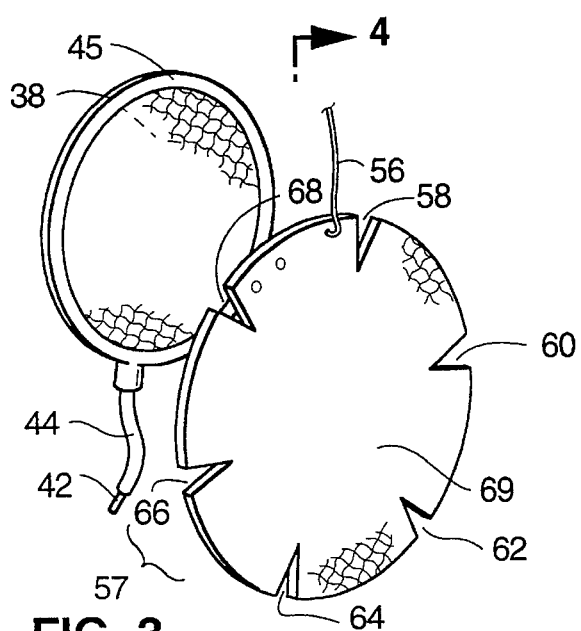
FIG. 3 is an exploded perspective view of a second preferred embodiment of a defibrillator electrode of the present invention.

FIG. 1 illustrates the placement of trocars for both observation and insertion of defibrillator electrodes between the pericardium and both the front and rear surfaces of the heart. In particular, a first opening 10, such as an incision or puncture is made in a patient 12 between the patient's 2nd rib and 6th rib. The exact location of the first opening 10 is dependent upon a patient's particular anatomy. Prior to the insertion of a trocar 14, the patient's left lung is deflated to allow unobstructed observation through the trocar 14. The left lung is deflated by drawing a vacuum through a tube which is inserted into the left lung of the patient 12. This tube is routed to the left lung either through the mouth or nose of the patient 12. A thoracoscope 16 then is inserted into the trocar 14 to permit observation by a surgeon through an eye piece 18 or through a video monitor which is connected to a video camera. In such a case, the video camera is optically coupled to the eye piece.

A second opening 20, such as an incision or puncture, which is subxiphoid, is then made and a second trocar 22 is inserted to point upward toward a pericardium 24. A third opening may be made and used for additional instrumentation or thoracoscopic observation as well as later placement of a chest drainage tube. As explained further herein, an endoscopic type grasping instrument 26 is utilized to insert a rolled defibrillator electrode through the second trocar 22 or simply through the opening 20 (without a trocar) to thereby position the defibrillator electrode 28. Such a positioned defibrillator electrode 30 is shown in phantom. An endoscopic type cutting instrument 32 is utilized, as explained further herein, to make an opening in the pericardium and to thereafter trim a tail 34 of the defibrillator electrode 28 after the electrode 28 has been secured within the patient 12.

By entering on the left side of the patient 12, access is gained to both the back side of the heart and the front side of the heart for defibrillator electrode placement.

Referring now to FIG. 2, there is shown an exploded perspective view of one embodiment of a defibrillator electrode 36 of the present invention. As will be appreciated by those skilled in the art, although the electrode shown in FIG. 2 is basically circular, a differently shaped electrode, for example an oval, may be utilized depending upon the precise electrical conduction characteristics desired of the electrode and of the physical shape and size of a particular patient's heart. The defibrillator electrode 36 consists of a platinum mesh 38 (only partially shown in FIG. 2) which attached to a silicone backing 40. As will be appreciated by those skilled in the art, although a platinum mesh is utilized in the preferred embodiments of the invention, other conductive materials which do not significantly interact with human tissue, may instead be utilized. The diameter of the platinum mesh 38 is substantially less than that of the silicone backing 40. Thus, when the platinum mesh 38 is substantially centered on the silicone backing 40, as detailed herein, a peripheral area 54 of the backing remains for attachment to the pericardium 24 by way of staples. In the preferred embodiment of the present invention, the silicone backing 40, which functions in part as an electrical insulator, is attached to the platinum mesh 38 with Silastic brand adhesive. Silastic brand adhesive is a silicone based adhesive which is available from Dow Corning Corporation of Midland, Mich. The adhesive is applied only to the junction of the periphery of the platinum mesh 38 and the silicone backing 40.

A conductor 42 is conductively attached to the platinum mesh 38 and this conductor 42 is encased within a silicone insulation 44. In the preferred embodiment of the invention, the conductor 42 extends onto platinum mesh 38 for a length of approximately 8 mm to thereby provide a sufficient electrical contact surface area between the lead wire 42 and the platinum mesh 38. A periphery 45 surrounds the platinum mesh 38. Titanium staples 46, 48, 50 and 52, as detailed further herein, are driven through the pericardium and into a peripheral area 54 of the silicone backing 40, to thereby fixedly secure the defibrillator electrode 36 between the pericardium and the heart. In normal use the ends of the titanium staples 46, 48, 50 and 52 are driven in a way to cause them to fold back toward the pericardium in the same manner as with as shipping carton staples. An Ethicon EMS Endoscopic Multifeed stapler can be utilized to automatically drive and fold back such staples. By driving the staples 46, 48, 50 and 52 into the peripheral area 54 of the silicone backing 40, away from platinum mesh 38, undesired changes in the conductive pattern of the platinum mesh 38 are prevented.

The defibrillator electrode 36 also includes a nylon tail 56, which corresponds to the tail 34 of FIG. 1. As detailed further herein, the tail 56 is attached to the peripheral area 54 and in use greatly facilitates the positioning and fixation of the defibrillator electrode 36. In the preferred embodiment of the invention the tail 56 is a multifilament nylon cord. Once the defibrillator electrode 36 has been inserted between the pericardium and the heart, the tail 56 can be pulled to further position the defibrillator electrode 36. Then, if desired, the tail 56 can be stapled to the pericardium to thereby allow a surgeon to pivot the defibrillator electrode 36 about the staple for further positioning.

Referring now to FIG. 3, a first alternative embodiment 57 of the defibrillator electrode 36 of FIG. 2 is shown. In FIG. 3 a set of notches 58, 60, 62, 64, 66 and 68 are positioned about the periphery of a silicone backing 69. Although FIG. 3 illustrates these notches to be V-shaped, it will be appreciated by those skilled in the art that the shape and number of such notches can be different. In addition, such notches may be placed unsymmetrically around the periphery of the silicone backing 69. The notches 58, 60, 62, 64, 66 and 68 allow the silicone backing 60 to more easily conform to a curved or spherical surface. Since the front and the rear of a human heart are semi-spherical, the defibrillator electrode 57 shown in FIG. 3, when placed between the pericardium and the heart, can more easily conform to the shape of the heart. As with the embodiment shown in FIG. 2, the diameter of the platinum mesh 38 is less than that of the silicone backing 69, to thereby provide a peripheral area of the silicone backing 69 into which staples may be driven.

Figure 4:
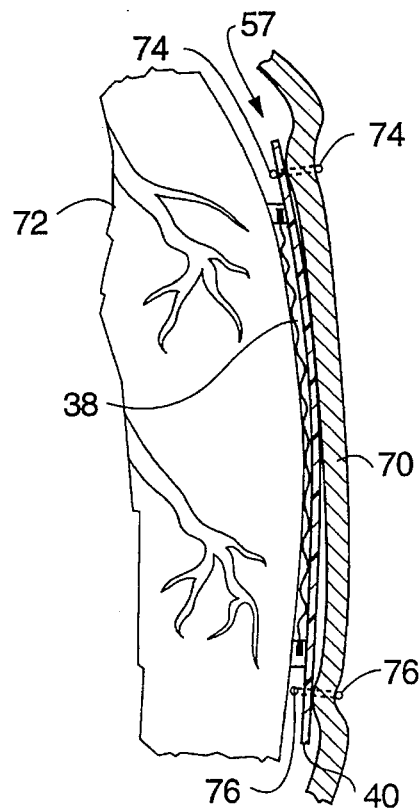
FIG. 4 is an assembled elevational sectional view taken along line 4—4 of FIG. 3 illustrating the placement of a defibrillator electrode between the pericardium and the heart.

Referring now to FIG. 4, the defibrillator electrode 57 is shown placed between a pericardium 70 and a heart 72. In the preferred embodiment of the invention, the silicone backing 69 is secured to the pericardium 70 by a staple 74 and a staple 76 and other staples which are not shown. The staples 74 and 76 are each driven through the pericardium 70 and through the peripheral area of silicone backing 69. The staples 74 and 76 are driven with an instrument (not shown) which causes the separate ends of the staples to fold over against that side of the silicone backing 69 which is adjacent to the heart 72. Such an arrangement not only holds the defibrillator electrode 57 more securely, but also minimizes the possibility of the staples touching the heart 72. Alternatively, the defibrillator electrode 57 may be secured to the pericardium 70 with sutures.

As illustrated in FIG. 4, the platinum mesh 38 of the defibrillator electrode 36 is generally in contact with the heart 72. The thickness of the silicone backing 69 is selected to accommodate the space between the pericardium 70 and the heart 72.

Figure 5:
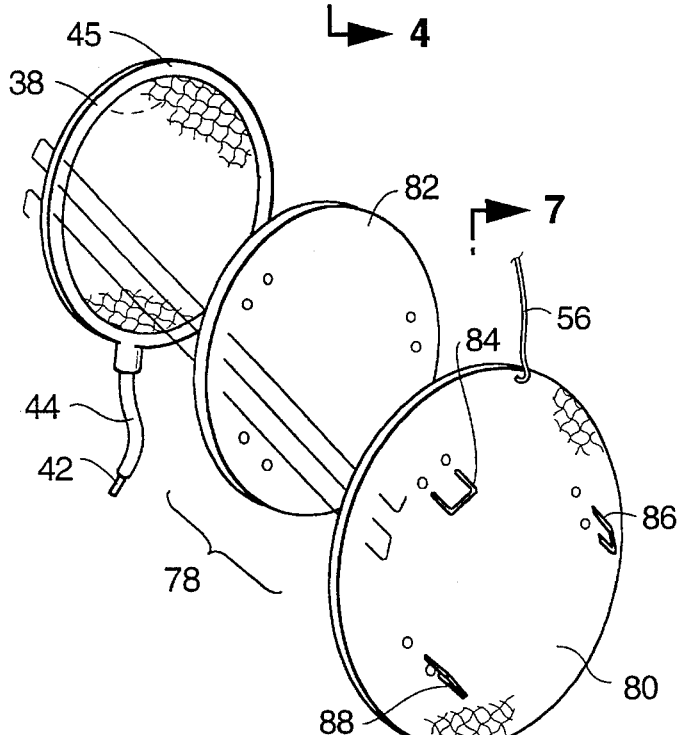
FIG. 5 is an exploded perspective view of a third embodiment of a defibrillator electrode of the present invention.

With reference now to FIG. 5, there is illustrated a second alternative embodiment 78 of a defibrillator electrode. The defibrillator electrode 78, as with both the defibrillator electrode 36 of FIG. 2 and the defibrillator electrode 57 of FIG. 3, includes the platinum mesh 38, the electrode wire 42 and the wire insulation 44. In contrast to the defibrillator electrode 36 of FIG. 2, however, the defibrillator electrode 78 includes a thin polypropylene mesh 80, which in the preferred embodiment of the invention is sewn onto a silicone spacer 82. The polypropylene mesh 80 also has attached to it the tail 56. As explained and illustrated further herein, after appropriate positioning between a heart and a pericardium, the defibrillator electrode 78 is secured with a set of staples 84, 86 and 88.

Figure 6:
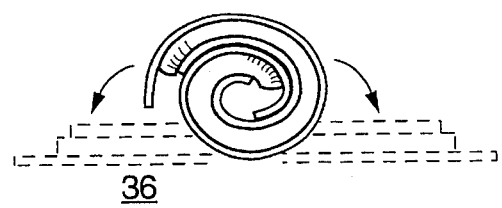
FIG. 6 is a transverse elevational view of the defibrillator electrode of FIG. 5, illustrating the defibrillator electrode in a coiled position.

Referring now to FIG. 6, the defibrillator electrode 36 of FIG. 2 is illustrated in a rolled state. After placement between a heart and a pericardium, the rolled defibrillator electrode with the assistance of a pair of forceps 26, is unrolled as illustrated in phantom in FIG. 6.

Figure 7:
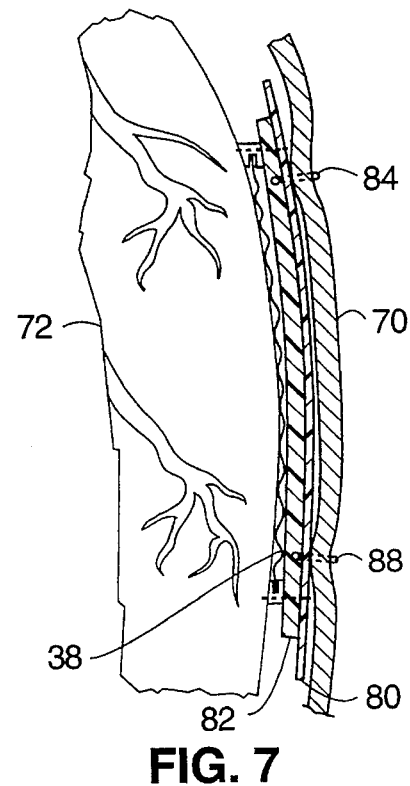
FIG. 7 is an assembled elevational section taken along line 7—7 of FIG. 5, illustrating the placement of the defibrillator electrode of FIG. 5 between the pericardium and a heart.

FIG. 7 illustrates the placement of the defibrillator electrode 78 of FIG. 5 between a heart 72 and a pericardium 70. As illustrated in FIG. 7, the staples 84 and 88 are driven through the pericardium 70 and are embedded into the silicone spacer 82. As also illustrated in FIG. 7, because the staples 84, 86 and 88 do not extend all the way through the silicone spacer 82, the defibrillator electrode 78 of FIG. 5 prevents contact between the staples 84, 86 and 88 and the heart 72 in the event of trauma which forces the pericardium 70 toward the heart 72.

In further detail, as the staples 84 and 88 have a length somewhat less than the sum of the thickness of the pericardium 70, the thickness of the polypropylene mesh 80 and the thickness of the silicone spacer 82. In the embodiment shown in FIG. 7, the staples 84 and 88 extend about half way through the silicone spacer 82.

Figure 8:
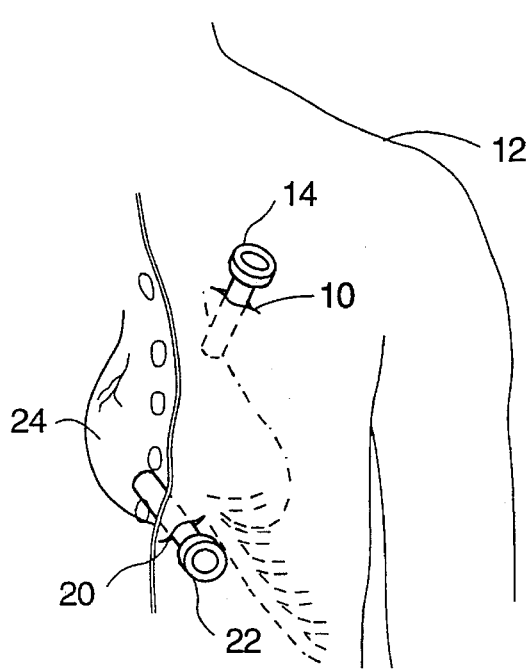
FIG. 8 is a diagrammatic perspective view illustrating the positioning of trocars in accordance with one of the methods of the present invention.

Referring now to FIG. 8, a first method for intrapericardial defibrillator electrode implantation is described in detail. The first opening 10 is made between the 2nd rib and 6th rib of a patient 12, the precise location dependent upon a particular patient's anatomy. The first trocar 14 is then inserted into the first opening 10. The second opening 20 is made subxiphoid and the second trocar 22 is inserted therein. The subxiphoid opening 20 is used for instrumentation and the insertion and manipulation of defibrillator electrodes.

Figure 10:
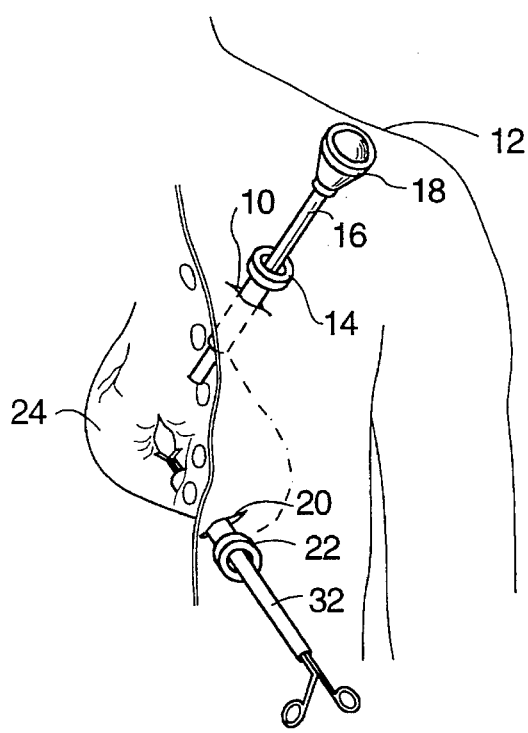
FIG. 10 is a diagrammatic perspective view illustrating a method of positioning a defibrillator electrode.

Referring now to FIG. 10, the thoracoscope 16 is inserted into the first trocar 14 to permit observation through the eyepiece 18 or through a video monitor which is connected to a video camera. In such a case the video camera is optically coupled to the eyepiece. The endoscopic type cutting instrument 32 is then inserted into the trocar 22 and is used to dissect the pericardium 24. The endoscopic type cutting instrument 32 is then removed from the trocar 22.

Figure 9:
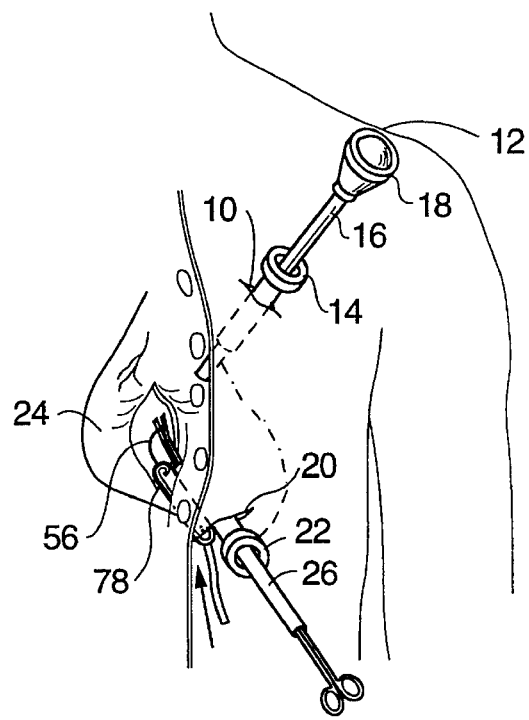
FIG. 9 is a diagrammatic perspective view illustrating a method of inserting a defibrillator electrode.

Referring now to FIG. 9, exterior to the patient 12 the endoscopic type grasping instrument 26, under the direct manipulation by a surgeon, grasps the tail 56 of a rolled defibrillator electrode 78. The endoscopic type grasping instrument 26 is then pushed through the second trocar 22 thereby pulling the tail of the rolled up defibrillator electrode 78 which in turn pulls the entire defibrillator electrode into the patient 12. In the alternative, the tail 34 of the defibrillator electrode 78 can be held, together with the rest of the defibrillator electrode 78, and then pushed through the second trocar 22 into the patient 12.

Figure 11:
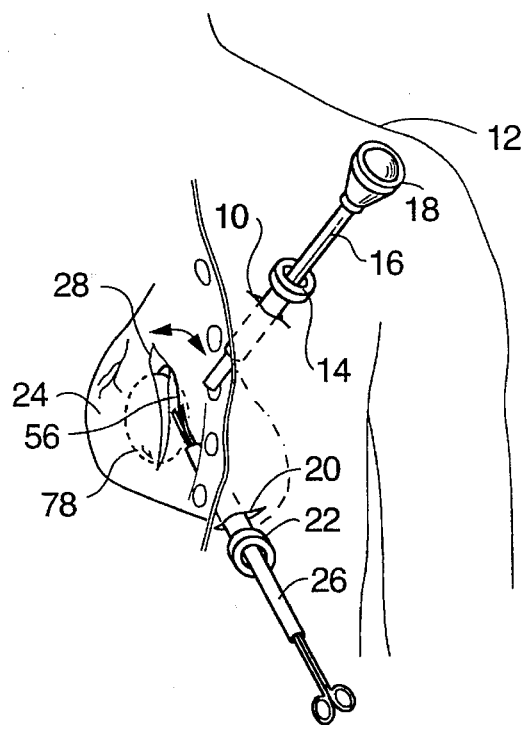
FIG. 11 is a diagrammatic perspective view illustrating a method of positioning a defibrillator electrode.
Figure 12:
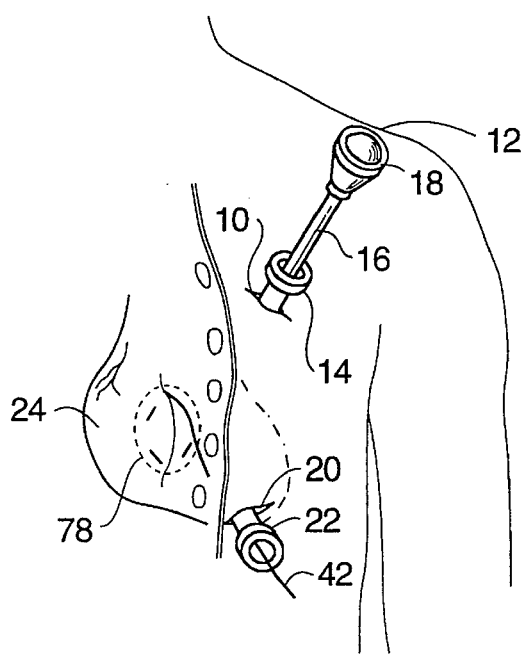
FIG. 12 is a diagrammatic perspective view illustrating a method of further positioning a defibrillator electrode.

With reference to FIG. 11, once the defibrillator electrode 78 has been pushed through the trocar 22 and into the pericardium 24, the defibrillator electrode 78 is released by the endoscopic type grasping instrument 26 to thereby allow the defibrillator electrode 78 to begin to unroll. To completely unroll the defibrillator electrode, it is generally necessary to utilize the endoscopic type grasping instrument 26 to manipulate the defibrillator electrode 78.

The defibrillator electrode 78 is then pulled into its approximate position, between the pericardium 24 and the heart. Under direct thoracoscopic vision, the base of the tail of the defibrillator electrode is fixed to the pericardium 24 with an endoscopic type surgical staple. The defibrillator electrode 78 is then manipulated by grasping the proximal conductor of the defibrillator electrode with the endoscopic type grasping tool 26. After optimum placement of the defibrillator electrode 78 has been determined by electrical testing, the defibrillator electrode is fixedly positioned by placing a second surgical staple through the pericardium 24 and through the peripheral area of the defibrillator electrode 78. Additional staples may be utilized, as previously described, to further secure the defibrillator electrode. After final testing, the excess portion of the tail 56 is removed from the defibrillator electrodes with the endoscopic type cutter 32. Alternatively, the defibrillator electrode 78 may be secured to the outside surface of the pericardium 24.

In order to connect the conductor 42 of the defibrillator electrode 78 to a defibrillator electronics module (not shown), which is implanted within the abdomen of a patient, a tunnel is dissected between the pericardium and the diaphragm from the subxiphoid opening toward the posterior aspect of the pericardium. In further detail, silicone tubing is utilized to tunnel from the abdomen up to one end of the trocar 22 adjacent to the subxiphoid opening 22. The silicone tubing is grasped with a endoscopic grasping tool 26 and is pulled out of the patient 12 up through the trocar 22. The silicone tubing is then secured to the conductor 42 and then pulled back through the trocar thereby routing the conductor down to the abdomen.

In some cases it may be desirable to attach the defibrillator electrodes on the outside of the pericardium instead of between the pericardium in the heart. In such cases, the defibrillator electrodes illustrated in FIGS. 2 and 3 would be used. With such placement, however, the amount of energy required to defibrillate is generally larger.

Figure 13:
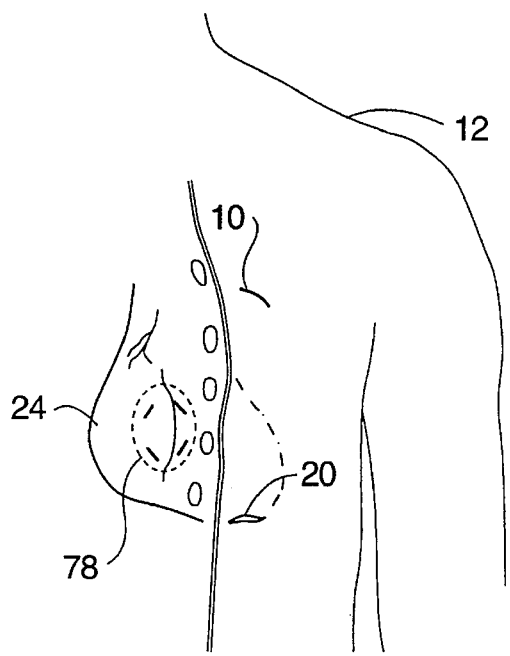
FIG. 13 is a diagrammatic perspective view illustrating one preferred placement of a defibrillator electrode.

FIG. 13 illustrates a final placement of the defibrillator electrode 78 between a pericardium 24 and a heart.

Figure 13A:
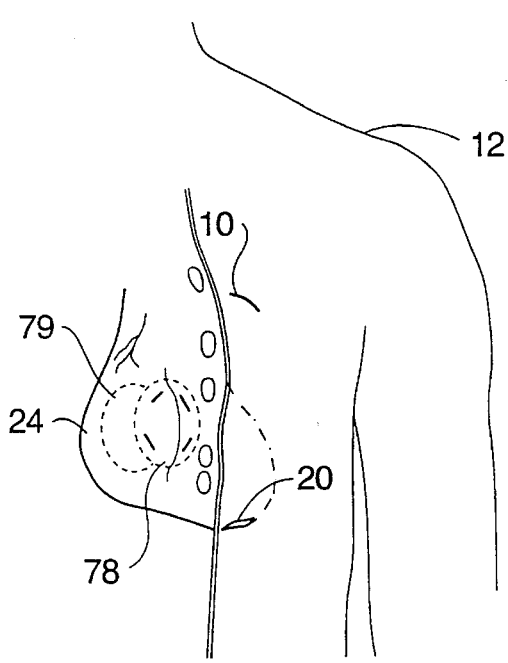
FIG. 13A is a diagrammatic perspective view illustrating the preferred placement of a pair of defibrillator electrodes.

With reference now to FIG. 13A, there is shown in phantom a second defibrillator electrode 79. The second defibrillator electrode 79 is implanted in the same manner as described, except that this second defibrillator electrode 79 is attached to the pericardium 24 to be positioned at to make contact with or near the rear side of the heart.

Figure 14:
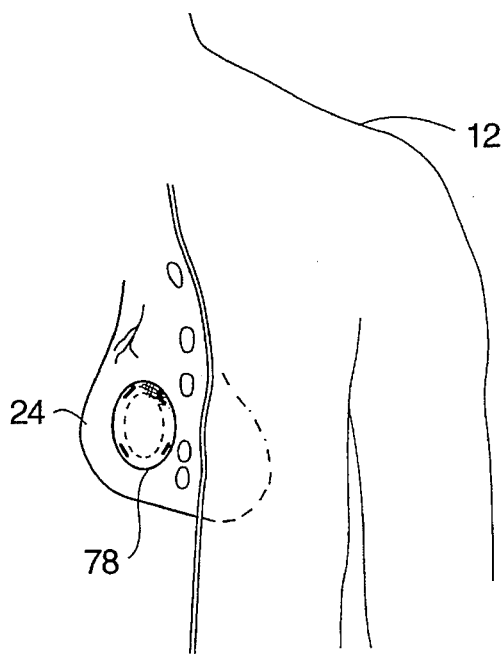
FIG. 14 is a diagrammatic perspective view illustrating the attachment of a defibrillator electrode to the pericardium.

FIG. 14 illustrates the final placement of the defibrillator electrode 78, after the openings 10 and 20 have healed.

Figure 15:
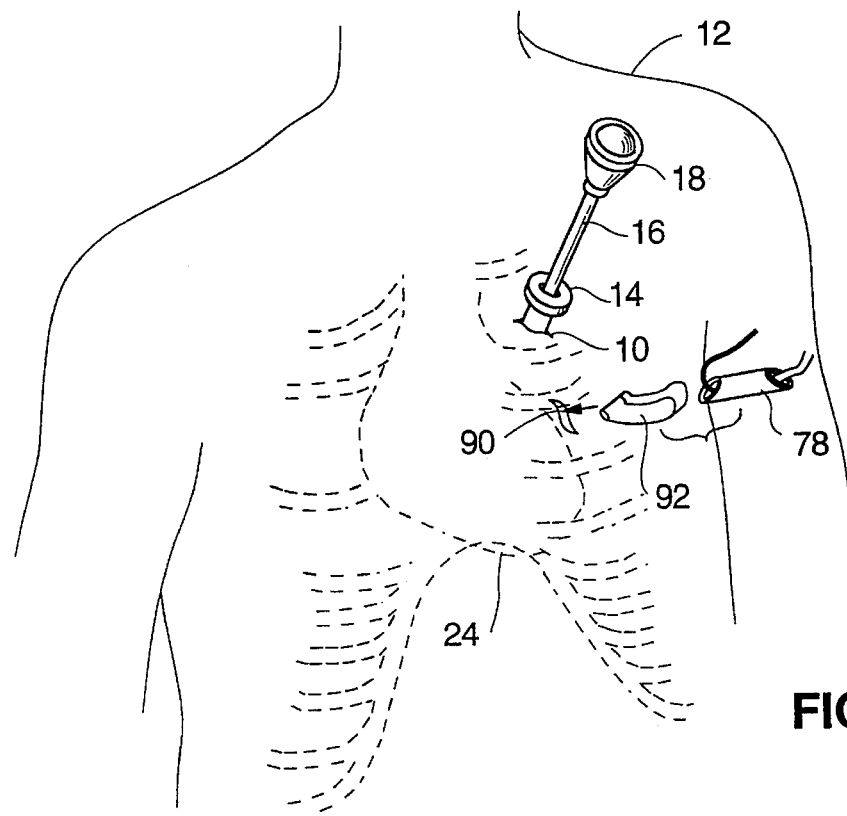
FIG. 15 is a diagrammatic perspective view illustrating an alternative method for the insertion and placement of a defibrillator electrode.

Referring now to FIG. 15, an alternate method for defibrillator electrode implantation is described. As with the first described method, the left lung of the patient 12 is first deflated. The opening 10 is made between the 2nd rib and the 6th rib of the patient 12. The exact location of the opening 10 is dependent upon a patient's particular anatomy. A trocar 14 is then inserted into the opening 10 and the thoracoscope 16 is inserted into the trocar 14 to permit observation.

A second opening 90 is then made between the ribs of the patient 12. The exact location of the second opening 90 is dependent upon a patient's particular anatomy; however, the second opening 90 is below the first opening 10. The defibrillator electrode 78 is rolled and placed into a flexible carrier 92. The flexible carrier 92 is then inserted through the second opening 90 using an endoscopic type grasping instrument (not shown). Once past the opening 90, the carrier 92 is pushed forward to release it from the defibrillator electrode 78. Then the carrier 92 is retracted through the opening 90. The exposed portion of the defibrillator electrode 78 is then grasped with an endoscopic type grasping tool and inserted either extrapericardial or intrapericardial as previously described. Because of the shape and flexibility of the carrier 92, the carrier 92 easily releases from the defibrillator electrode 78 when the defibrillator electrode 78 is pushed completely through the opening 90. Placement of the defibrillator electrode 78 and fixation thereof is performed as previously described with reference to FIGS. 8 through 13 except that such placement and fixation is performed without the benefit of a trocar.

Figure 15B:
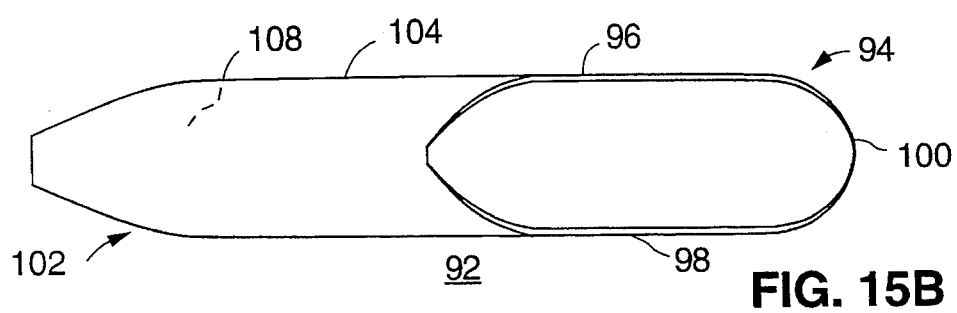
FIG. 15B is a top perspective view of the defibrillator electrode carrier of FIG. 15A.
Figure 15A:
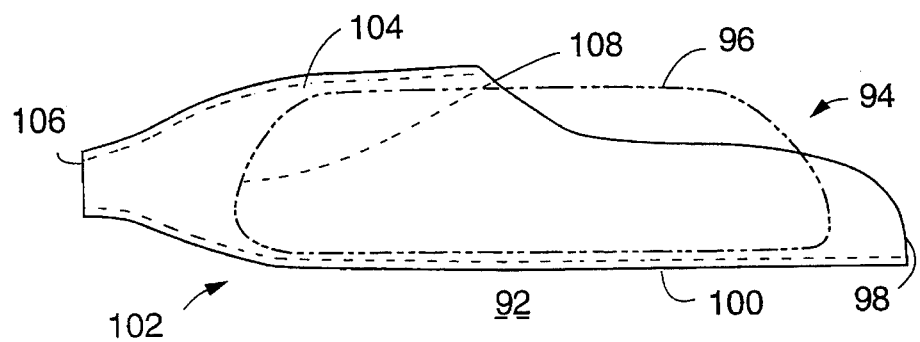
FIG. 15A is a side perspective view of a defibrillator electrode carrier.
Figure 15C:
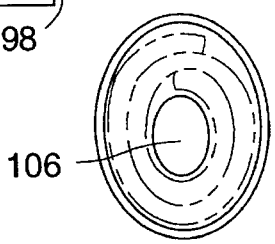
FIG. 15C is an end view of the defibrillator electrode carrier of FIG. 15A.

Referring now to FIGS. 15A, 15B and 15C, there is shown in greater detail the flexible carrier 92. In the preferred embodiment of the invention, the flexible carrier 92 consists of a partially enclosed area 94 having a first wall 96, a second wall 98 and a floor 100 therebetween.

The floor 100 extends the entire length of the flexible carrier 92 from one end of the partially enclosed area to a tapered region 102. The tapered region 102 is connected to an enclosed region 104.

A narrow end 106 of the carrier 92 is open as illustrated in FIG. 15C. In the preferred embodiment of the invention, the flexible carrier 92 is molded from either silicon or other waterproof surgically compatible material.

A second alternate method for defibrillator electrode placement is performed as illustrated in FIGS. 16 through 19. Referring to FIG. 16, a first handle 110 and a second handle 112, each having a slot or recess 114 and 116 respectively at one end, are utilized to grasp a defibrillator electrode 118. As illustrated in FIGS. 16, opposite sides of the defibrillator electrode 118 are inserted at into the slots 114 and 116 of the first handle 110 and the second handle 112 respectively, so that conductor within the insulation 120 is relatively parallel to each of the first and second handles 110 and 112.

Referring now to FIG. 17, the first and second handles 110 and 112 are then turned toward each other to thereby roll the defibrillator electrode 118 into two connected rolled segments. The result is very compact bundle that can be inserted into the patient 12 through a small diameter opening.

Referring now to FIG. 18, after the defibrillator electrode 118 has been rolled, the handles 110 and 112 are used to insert the defibrillator electrode 118 through a subxiphoid opening 122. Once the defibrillator electrode is in approximately the desired position, as illustrated in FIG. 19 and as viewed through the eyepiece 18, the handles 110 and 112 are rotated away from each other to thereby unroll the defibrillator electrode 118. The handles 110 and 112 are then pulled away from the defibrillator electrode 118 out through the subxiphoid opening 122. The defibrillator electrode 118 may then be repositioned and secured as described with respect to FIGS. 8 through 14.

FIGS. 1 through 19 of the drawing depict various preferred embodiments of the present invention for purposes of illustration only. One skilled in the art will readily recognize from the specification, drawing and abstract that incisions and punctures are but two methods of creating an opening, and that alternative embodiments of the methods and structures illustrated herein may be employed without departing from the principals of the invention described herein.

We claim:

1. An implantable defibrillator electrode, comprising:

a flexible conductive mesh having at least one side;

a flexible conductive wire conductively attached to the flexible conductive mesh;

a flexible insulator affixed to one side of the flexible conductive mesh, the flexible insulator having a surface extending beyond a periphery of the flexible conductive mesh; and a tail attached to said surface extending beyond the periphery of the flexible conductive mesh.

2. The implantable defibrillator electrode of claim 1, wherein the tail comprises:

a flexible cord.

3. The implantable defibrillator electrode of claim 1, wherein the attachment of the flexible conductive wire to the flexible conductive mesh is opposite to the attachment of the tail to the surface extending beyond the periphery of the flexible conductive mesh.

4. The implantable defibrillator electrode of claim 1 wherein the flexible conductive mesh comprises:

platinum wire.

5. The implantable defibrillator electrode of claim 1 wherein the flexible insulator comprises:

silicone.

6. An implantable defibrillator electrode, comprising:

a flexible conductive mesh having at least one side;

a flexible conductive wire conductively attached to the flexible conductive mesh;

a flexible insulator affixed to one side of the flexible conductive mesh, the flexible insulator having a surface extending beyond a periphery of the flexible conductive mesh; and a tail attached to the flexible insulator, wherein the tail comprises a flexible multifilament nylon cord.

7. An implantable defibrillator electrode, comprising:

a flexible conductive mesh having at least one side;

a flexible conductive wire conductively attached to the flexible conductive mesh;

a flexible insulator affixed to one side of the flexible conductive mesh, the flexible insulator having separate regions extending beyond a periphery of the flexible conductive mesh; and a tail attached to at least one of the separate regions.

8. The implantable defibrillator electrode of claim 7, wherein the tail comprises:

a flexible cord.

9. An implantable defibrillator electrode, comprising:

a round flexible conductive mesh;

a flexible conductive wire conductively attached to the round flexible conductive mesh; and a flexible insulator having a periphery, the flexible insulator affixed to one side of the flexible conductive mesh, the flexible insulator having a surface extending beyond a periphery of the flexible conductive mesh, the flexible insulator further having at least one notch at its periphery.

10. The implantable defibrillator electrode of claim 9 wherein said notch is wedge shaped.

11. An implantable defibrillator electrode, comprising:

a flexible conductive mesh;

a flexible conductive wire conductively attached to the flexible conductive mesh;

a flexible nonconductive mesh; and a flexible insulator, wherein the flexible insulator is secured to a surface of each of the flexible conductive mesh and the flexible nonconductive mesh and the flexible insulator is between the flexible conductive mesh and the flexible nonconductive mesh.

12. The implantable defibrillator electrode of claim 11 further comprising:

a tail attached to the flexible nonconductive mesh.

13. An implantable defibrillator electrode, comprising:

a flexible conductive mesh;

a flexible conductive wire conductively attached to the flexible conductive mesh;

a flexible nonconductive mesh; and a flexible insulator, the flexible insulator secured to the flexible conductive mesh and the flexible nonconductive mesh, wherein the flexible insulator is between the flexible conductive mesh and the flexible nonconductive mesh and wherein the flexible nonconductive mesh includes a surface extending beyond a periphery of the flexible insulator.

14. An implantable defibrillator electrode, comprising:

a flexible conductive mesh having at least one side;

a flexible conductive wire conductively attached to the flexible conductive mesh;

a flexible insulator affixed to one side of the flexible conductive mesh, the flexible insulator having a surface extending beyond a periphery of the flexible conductive mesh; and a tail attached to the flexible insulator, wherein the tail comprises a non-conductive flexible cord.

* * * * *

UNITED STATES PATENT AND TRADEMARK OFFICE
CERTIFICATE OF CORRECTION

PATENT NO. : 5,464,447
DATED : November 7, 1995
INVENTOR(S) : Thomas J. Fogarty, Portola Valley, Thomas A. Howell, Palo Alto, It is certified that error appears in the above-indentified patent and that said Letters Patent is hereby corrected as shown below:

On the title page: Item [73]

Assignee: Sony Corporation, Japan assignee information should read as follows:

Assignee: Thomas J. Fogarty, Portola Valley, California

Signed and Sealed this

Twelfth Day of November, 1996

Attest:

BRUCE LEHMAN

Attesting Officer     Commissioner of Patents and Trademarks